United States Patent [19]
Williamson et al.

[11] Patent Number: 5,800,551
[45] Date of Patent: Sep. 1, 1998

[54] APPARATUS AND METHOD FOR SHOULDER ARTHROPLASTY

[75] Inventors: Daniel E. Williamson; Connie P. Marchek; Lance Dean Perry, all of Warsaw, Ind.

[73] Assignee: Biomet, Inc., Warsaw, Ind.

[21] Appl. No.: 814,940

[22] Filed: Mar. 10, 1997

[51] Int. Cl.$^6$ .................................................. A61F 2/40
[52] U.S. Cl. .................................................. 623/19; 623/18
[58] Field of Search ........................... 623/18, 19, 22

[56] References Cited

U.S. PATENT DOCUMENTS

| | | |
|---|---|---|
| 2,910,978 | 11/1959 | Urist . |
| 3,803,641 | 4/1974 | Golyakhovsky . |
| 3,916,451 | 11/1975 | Buechel et al. . |
| 4,042,980 | 8/1977 | Swanson . |
| 4,045,825 | 9/1977 | Stroot . |
| 4,045,826 | 9/1977 | Stroot . |
| 4,206,517 | 6/1980 | Pappas et al. . |
| 4,355,429 | 10/1982 | Mittelmeier et al. . |
| 4,865,605 | 9/1989 | Dines et al. ............................. 623/19 |
| 4,883,490 | 11/1989 | Oh ........................................... 623/22 |
| 4,964,865 | 10/1990 | Burkhead et al. ....................... 623/19 |
| 4,964,867 | 10/1990 | Boger ....................................... 623/20 |
| 5,030,219 | 7/1991 | Matsen, III et al. .................... 606/80 |
| 5,032,132 | 7/1991 | Matsen, III et al. .................... 623/19 |
| 5,370,694 | 12/1994 | Davidson ................................ 623/22 |
| 5,489,310 | 2/1996 | Mikhail .................................. 623/19 |

FOREIGN PATENT DOCUMENTS

| | | |
|---|---|---|
| 2377798 | 9/1978 | France . |
| 2418644 | 11/1979 | France . |
| 2041929 | 10/1980 | Germany . |

OTHER PUBLICATIONS

"The Cofield Total Shoulder System", 1989, by Richards Medical Company, pp. 1–5.
"The Foundation Total Shoulder System", 1996, by Encore Orthopedics, Inc., catalog #0190–100.

*Primary Examiner*—Randy C. Shay
*Attorney, Agent, or Firm*—Harness, Dickey & Pierce, P.L.C.

[57] ABSTRACT

A glenoid component for use in shoulder arthroplasty which is adapted to be implanted into a scapula and engaged by a head of a humeral component. The glenoid component includes a body having a first articulating surface and second textured medial surface opposite to the first articulating surface. The first articulating surface is adapted to be engaged by the head of the humeral component and the second textured medial surface is adapted to be secured to the scapula. A plurality of circular base members extends from the second textured medial surface and provides a circular base pad having a first diameter. A plurality of cylindrical pegs each have a first end adapted to engage a cavity formed in the scapula and a second end extending from one of the circular base members. Each of the cylindrical pegs is partially defined by a sidewall having a second diameter such that the first diameter of the cylindrical base pads is larger than the second diameter of the cylindrical pegs to increase peg shear strength.

27 Claims, 4 Drawing Sheets

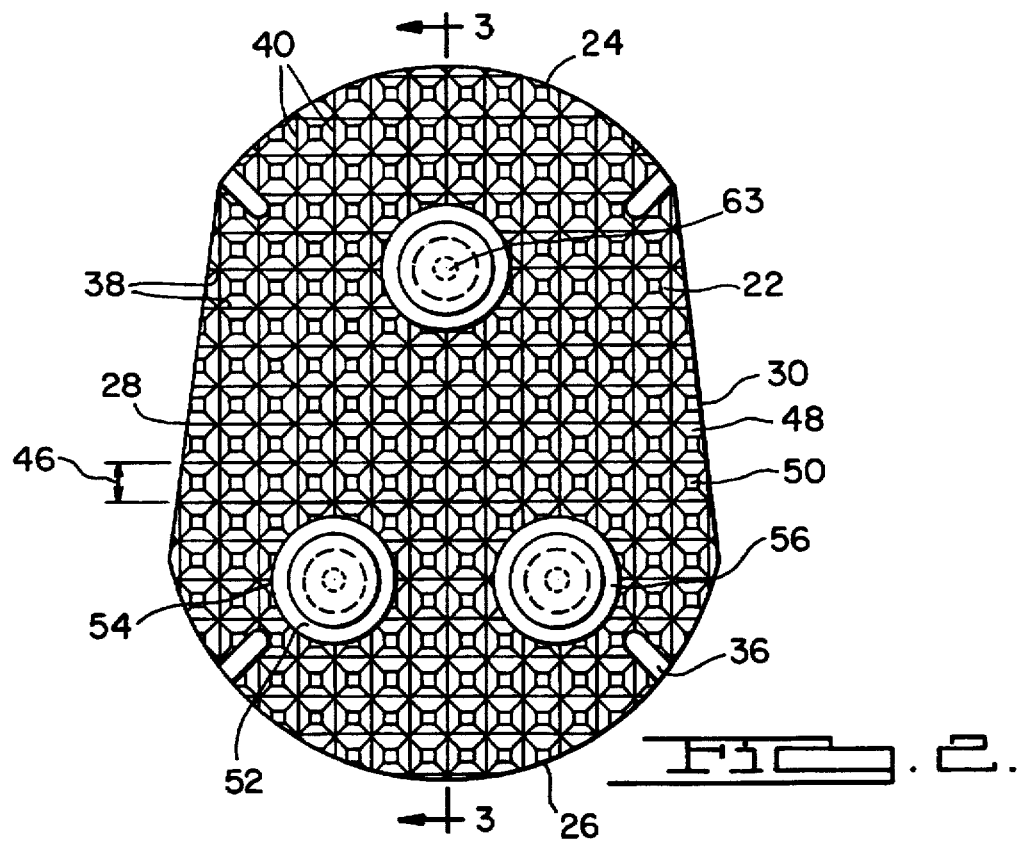
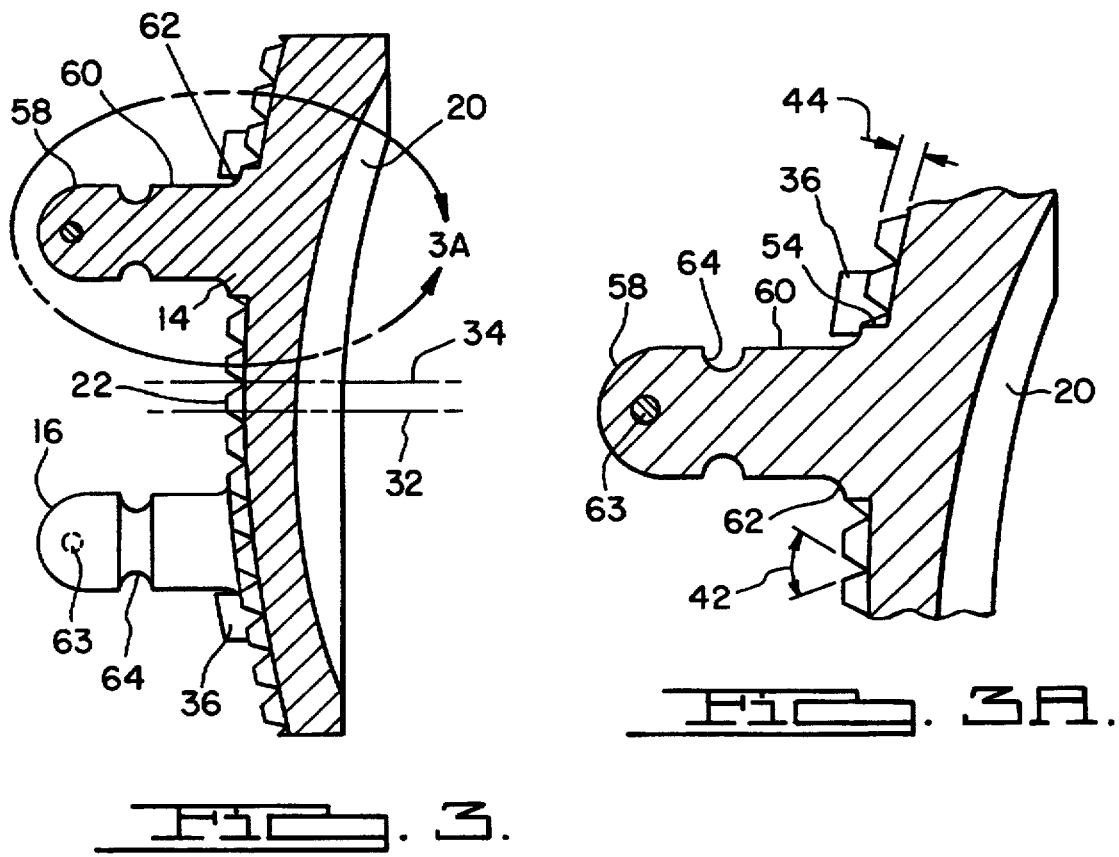

APPARATUS AND METHOD FOR SHOULDER ARTHROPLASTY

BACKGROUND OF THE INVENTION

1. Field of the Invention

This invention relates generally to an apparatus and method for shoulder arthroplasty and, more particularly, to a glenoid component and other associated surgical components and instruments for use in shoulder arthroplasty.

2. Discussion of the Related Art

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus is resected and a cavity is created in the intramedullary canal of the host humerus for accepting a humeral component. The humeral component includes a head portion used to replace the natural head of the humerus. Once the humeral component has been implanted, the glenoid cavity positioned at the scapula head may also be resurfaced and shaped to accept a glenoid component. The glenoid component generally includes an articulating surface which is engaged by the head portion of the humeral component.

It is generally known in the art to provide a shoulder joint prosthesis having a glenoid component, as discussed above. However, the current prior art glenoid components along with the associated surgical components and instruments utilized during shoulder arthroplasty suffer from many disadvantages.

For example, since the glenoid component is subject to various types of loading by the head portion of the humeral component, the glenoid component must offer a stable and secure articulating surface. To achieve this, some glenoid components provide a keel attached to the medial surface of the glenoid component. However, such a keeled glenoid component may not offer stability in the inferior/superior direction, thereby potentially increasing the tendency for the glenoid component to rock and loosen when loaded. Moreover, the size and shape of the keel requires a groove to be shaped into the scapula which is very labor intensive and time consuming. Additionally, the shape of the groove also requires an excess of bone tissue to be removed from the glenoid, thereby potentially weakening the end of the natural glenoid in some patients.

Other prior art glenoid components utilize multiple pegs which are inserted and cemented into holes bored into the glenoid cavity. However, such existing pegged glenoid components also exhibit several disadvantages. For example, some of the pegged glenoid components utilize up to five pegs to stabilize and secure the glenoid component to the scapula. Such glenoid components increase the amount of bone tissue removed, while also increasing the labor and complexity of the shoulder arthroplasty. Other pegged glenoid components may offer one or two larger diameter pegs which reduces the complexity of the shoulder arthroplasty. However, the larger diameter pegs also requires excess bone tissue to be removed which may not be practical in some patients. Furthermore, the use of one or two pegs may potentially reduce overall stability of the glenoid component, similar to a keeled glenoid.

Additionally, most prior art glenoid components only rely on the keel or pegs to secure the glenoid component to the scapula, via a cement mantle. The keel or pegs may also include grooves or holes which act as an anchor once the keel or pegs are cemented within the glenoid cavity. The medial surface of most glenoid components are thus generally overlooked to enhance cement fixation and are therefore generally smooth. Although, some glenoid components may include a few longitudinal grooves and others may include both grooves and depressions on the medial surface. However, such surface enhancements only utilize or texture a portion of the medial surface, thereby not advantageously using the entire medial surface. Moreover, such glenoid components do not provide for a uniform cement mantle at the medial surface.

What is needed then is a glenoid component and associated surgical components for use in shoulder arthroplasty which does not suffer from the abovementioned disadvantages. This in turn, will provide a glenoid component which is stable and secure, reduces the overall amount of bone tissue required to be removed, reduces the overall surgical time and complexity, increases overall medial surface area, enhances and increases peg strength without increasing overall peg diameter, provides a fully enhanced or textured medial surface for enhanced cement fixation and increased overall stability, provides for a uniform cement mantle, and provides increased tensile and shear strength. It is, therefore, an object of the present invention to provide such a glenoid component and associated surgical components for use in shoulder arthroplasty.

SUMMARY OF THE INVENTION

In accordance with the teachings of the present invention, an apparatus and method for shoulder arthroplasty is disclosed. The apparatus and method employs a glenoid component and other associated surgical components for use in the shoulder arthroplasty. In this regard, the glenoid component is adapted to be implanted into a scapula at the glenoid fossa or cavity and engaged by a head portion of a humeral component.

In one preferred embodiment, a glenoid component is used for shoulder arthroplasty such that the glenoid component is adapted to be implanted into a scapula and engaged by a head of a humeral component. The glenoid component includes a body having a first articulating surface and a second textured medial surface which is opposite to the first articulating surface. The first articulating surface is adapted to be engaged by the head of the humeral component and the second textured medial surface is adapted to be secured to the scapula. A plurality of circular base members extend from the second medial textured surface such that each of the circular base members provides a circular base pad having a first diameter. A plurality of cylindrical pegs each have a first end adapted to engage a cavity formed in the scapula and a second end extending from one of the circular base members. Each of the cylindrical pegs is partially defined by a sidewall having a second diameter, such that the first diameter of the circular base peg is larger than the second diameter of the cylindrical peg to increase peg shear strength without having to enlarge the cavity formed in the scapula to accommodate a larger second diameter.

Use of the present invention provides an apparatus and method for shoulder arthroplasty, and specifically, a glenoid component and associated surgical components for use in shoulder arthroplasty. As a result, the aforementioned disadvantages associated with the currently available glenoid components and associated surgical components for shoulder arthroplasty have been substantially reduced or eliminated.

BRIEF DESCRIPTION OF THE DRAWINGS

Still other advantages of the present invention will become apparent to those skilled in the art after reading the following specification and by reference to the drawings in which:

FIG. 2 is a top planar view of the glenoid component of FIG. 1;

FIG. 3 is a side cross-sectional view of the glenoid component taken along line 3—3 of FIG. 2;

FIG. 3A is an enlarged side cross-sectional view of the glenoid component taken about line 3A of FIG. 3.

DETAILED DESCRIPTION OF THE PREFERRED EMBODIMENT(S)

The following description of the preferred embodiment concerning an apparatus and method for shoulder arthroplasty is merely exemplary in nature and is in no way intended to limit the invention or its applications or uses.

Figure 1:
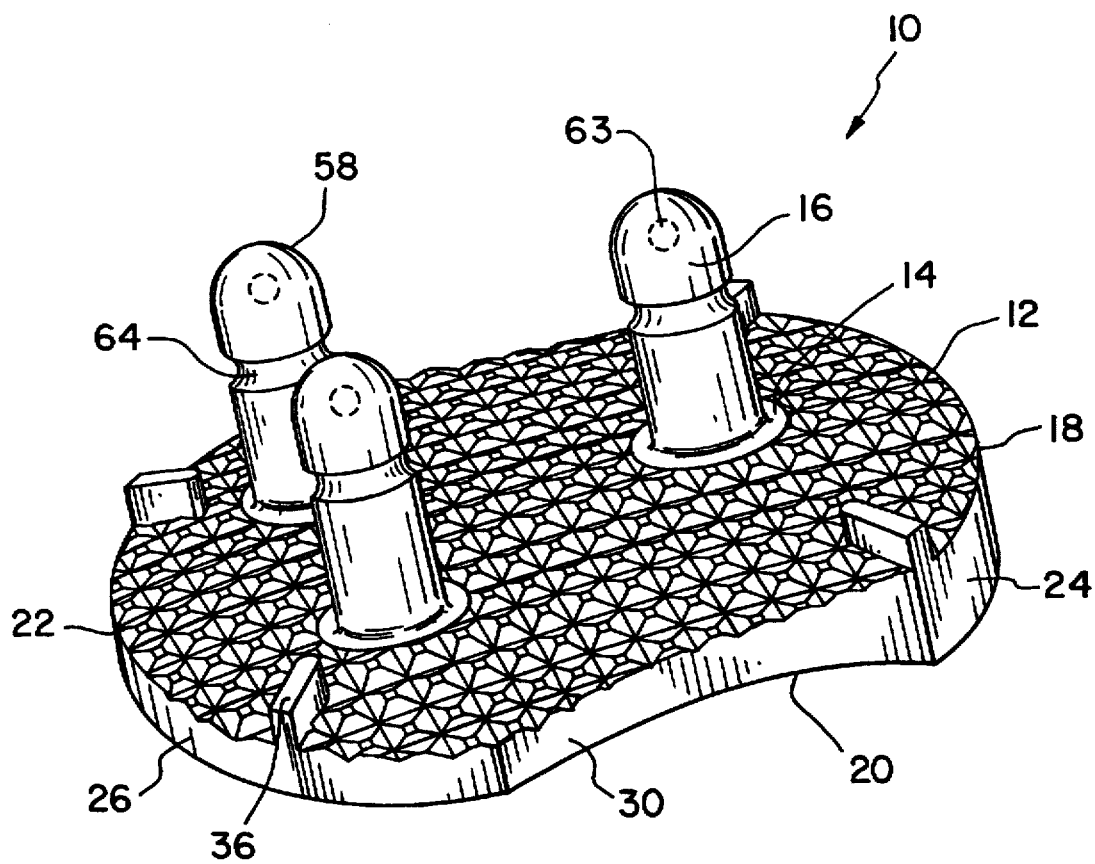
FIG. 1 is an enlarged perspective view of a glenoid component according to the teachings of a preferred embodiment of the present invention.

Referring to FIG. 1, a perspective view of a glenoid component 10 according to the teachings of a preferred embodiment of the present invention is shown. The glenoid component 10 includes a body 12, three (3) base members 14 and three (3) fixation pegs 16. The glenoid component 10 is preferably made from ultra-high molecular weight polyethylene (UHMWPE) or other suitable implantable material. The dimensions of the glenoid component 10 discussed herein are for a medium sized glenoid component 10. Those skilled in the art will recognize that larger or smaller glenoid components 10 may also be used depending on the patient's size and that the dimensions provided herein are merely for exemplary purposes.

The body 12 is defined by an outer peripheral sidewall 18, a first articulating arcuate or spherical surface 20 and a second textured medial surface 22. The outer peripheral sidewall 18 is generally pear-shaped and includes a curved superior portion 24 having a radius of about 0.58 inches, a curved inferior portion 26 having a radius of about 0.55 inches, a first planar portion 28 and a second planar portion 30. The widest portion of the body 12 is about 1.0 inch and the longest portion of the body is about 1.35 inches. The superior portion 24 of the sidewall 18 has a thickness of about 0.24 inches which narrows to a thickness of about 0.15 inches at the inferior portion 26 such that superior dislocation is minimized.

The articulating arcuate or spherical concave surface 20 of the glenoid component 10 is designed to permit both rotational and translational movement of a head of a humeral component. The center 32 of the curvature or sphere of the articulating surface 20 is inferior to the center 34 of the glenoid component 10, as shown clearly in FIG. 3. This offset curvature or sphere provides for the thicker superior region or portion 24. The curvature or sphere has a spherical concave arc defined by a radius of about 1.5 inches from the offset center 32. The offset center 32 is offset by about 0.1 inches from the center 34 of the glenoid component 10.

The medial textured surface 22 has an overall spherical convex arc defined by a radius of about 3.0 inches from the center 34. The medial textured surface 22 includes an enhanced textured surface over substantially the entire medial textured surface 22. The medial textured surface 22 includes a first plurality of parallel grooves 38 positioned substantially perpendicular to a second plurality of parallel grooves 40, similar to a checkerboard or waffle. The grooves 38 and 40 have an angle 42 of about 60°, a depth 44 of about 0.04 inches, and a separation 46 of about 0.075 inches. The grooves 38 and 40 essentially form a plurality of truncated pyramids 48 having a substantially square arcuate top 50 formed by an arc of about 0.03 inches in width and length.

The textured or waffle surface 22 defined by the truncated pyramids 48 substantially increases the overall medial surface area. As a result, cement adhesion is significantly increased between the medial textured surface 22 and the scapula due to the waffle texture of surface 22. The angle 42 of the grooves 38 and 40 also enables cement to more easily fill the entire grooves 38 and 40 as compared to grooves having a perpendicular edge. Moreover, both the shear strength and fixation (tensile) strength are greatly increased as compared to conventional smooth glenoid medial surfaces. It should further be noted that conventional smooth glenoid medial surfaces generally do not utilize a cement mantle between the smooth medial surface and the scapula. In contrast, the glenoid component 10 provides for a cement mantle between the medial surface 22 and the scapula, thereby increasing the overall stability and securement of the glenoid component 10 to the scapula.

To insure that there is a uniform cement mantle, four (4) removable medial cement spacers 36 are utilized. Each medial cement spacer 36 forms an elongated rectangle which is formed into the medial textured surface 22 at four corner positions around the outer peripheral sidewall 18. Each medial cement spacer 36 extends above the medial textured surface 22 by about 1 millimeter to ensure there is a sufficiently uniform and thick cement mantle. This uniform cement mantle further increases fixation of the glenoid component 10 to the scapula. Should it be desired to not utilize the medial cement spacers 36, the medial cement spacers may simply be removed from the medial textured surface 22 by cutting or trimming the medial cement spacers 36 using an appropriate cutting tool.

Each circular base member 14 extends from the medial textured surface 22 to define or fill-in a smooth circular base pad 52 having a diameter of about 0.25 inches. Each base member 14 also includes a sidewall 54 formed within and from the medial textured surface 22. Each circular pad 52 provides a smooth flat surface for which each cylindrical peg 16 extends out from leaving an annular portion 56. Each larger diameter circular pad 52 reduces or eliminates any stress risers about each cylindrical peg 16 which could be caused by positioning the medial textured surface 22 immediately adjacent to the cylindrical pegs 16.

Each cylindrical fixation peg 16 has a diameter of about 0.185 inches and is positioned concentric with a base member 14. One of the pegs 16 is positioned superior to the center 34 of the glenoid component 10 and the two remaining pegs 16 are positioned inferior to the center 34 of the glenoid component 10. As shown in FIG. 2, the pegs 16 are positioned to form the corners of an isosceles triangle which provides for both rotational and translational stability with the minimal amount of pegs 16, thereby reducing the overall amount of bone tissue removed from the glenoid cavity of the scapula.

Each peg 16 includes a first end 58 which is inserted into or engages a cavity or hole formed within the glenoid cavity of the scapula and a second end 60 which extends from or is formed integral with the base member 14. The first end 58 is semi-spherical and the second end 60 has a 0.03 radius 62 about the circumference of the second end 60 of the peg 16 which blends into the flat or smooth portion of the circular pad 52 or annular portion 56 to decrease the overall shear stress of the peg 16. Embedded within the first end 58 of each peg 16 is a tantalum ball 63. The tantalum balls 63 enable the glenoid component 10 to be easily identified in an x-ray. Each peg 16 further includes an outbound groove 64 about the circumference of the peg 16 having a radius of about 0.032 inches, a width of about 0.064 inches which creates a narrow diameter of about 0.12 inches within the cylindrical peg 16. The circumferential grooves 64 provide a locking mechanism between the glenoid component 10 and the glenoid cavity of the scapula, via a cement mantle.

The length of each peg 16 is about 0.37 inches and each are designed to be greater than or equal to twice the peg diameter. The larger diameter base member 14 along with the radius 62 about the end 60 enables a smaller overall diameter peg 16 to be utilized without sacrificing overall shear peg strength. In other words, if the base member 14 were not utilized, a larger diameter peg 16 would be required to achieve similar shear strengths. By utilizing the larger diameter base member 14 with the smaller diameter peg 16, the amount of bone tissue removed from the glenoid cavity of the scapula or the size of the holes bored into the glenoid cavity of the scapula is also reduced. Therefore, additional bone tissue is not required to be removed, as compared to utilizing a larger diameter peg without the base member 14. Moreover, by reducing the amount of bone tissue removed from the glenoid cavity of the scapula, the overall strength of the scapula is also increased where the glenoid component 10 engages the scapula.

The method for implanting the glenoid component 10 along with the associated surgical components utilized, will now be described with reference to FIGS. 4A–4D. Initially, if a total shoulder arthroplasty is performed, a humeral component 66 having a head portion 68 (see FIG. 4D) is generally first implanted into the humerus of the patient using techniques well known in the art. The humeral component 66 is preferably of the type disclosed in U.S. Pat. No. 4,865,605, which is hereby incorporated by reference, or other suitable conventional humeral component. Once the humeral component 66 is implanted into the humerus, glenoid preparation begins. With the glenoid cavity 70 of the scapula 72 exposed, an alignment or pilot hole 74 is first drilled substantially in the center of the glenoid cavity 70 using a 0.157 inch quick release drill bit 76 and a driver 78.

Once the hole 74 is drilled, the glenoid cavity 70 is reamed using a glenoid surface rasp 80 and an angled reamer shaft 82 with driver 78. The glenoid surface rasp 80 includes a guide pin 84 and a roughened spherical surface 86 substantially corresponding to the spherical shape of the medial surface 22 of the glenoid component 10. The guide pin 84 is inserted into the hole 74 and a threaded finger 88 of the rasp 80 rotatably secures the rasp 80 to the angled reamer shaft 82. The angled reamer shaft 82 includes an internal flexible and rotatable drive shaft 90 and an external angled housing 92. The angled reamer shaft 82 permits rasping or drilling in tight glenoid cavities 70. Upon rotating the surface rasp 80, the bone of the glenoid cavity 70 is prepared to mate or conform with the shape of the medial surface 22 of the glenoid component 10.

Once the surface of the glenoid cavity 70 has been prepared, a drill guide 94 is employed as a template to locate drill positions for the pegs 16. The drill guide 94 includes a knurled handle 96 and opposing drill templates 98 located on opposite ends of the knurled handle 96. The drill templates 98 are affixed to the handle 96 by a weld or other opposite fixation means. Each drill template 98 has an outer peripheral shape which is substantially similar to the outer peripheral sidewall 18 of the glenoid component 10. Each drill template 98 includes a pointed plug or cruciate 100 located on a spherical medial side 102 of each drill template 98. The cruciate 100 has a larger cross-sectional size than the diameter of the pilot hole 74. The cruciate 100 thereby cuts into the bone tissue as the cruciate 100 is inserted into the pilot hole 74. This action secures the drill guide 94 to the scapula 72, thus preventing rotation of the drill template 98 when drilling the holes for the pegs 16. Each drill template 98 is affixed on both ends of the knurled handle 96 in an angled manner such that either drill template 98 on either end of the drill guide 94 may be employed depending on whether a right or left shoulder arthroplasty is being performed or a left or right handed surgeon is utilizing the drill guide 94.

Once the cruciate 100 of the drill guide 94 is inserted into the hole 74, thereby securely positioning the drill guide 94 relative to the scapula 72, a superior hole 104 is first drilled using a 0.25 inch diameter drill bit 106 in conjunction with either the angled reamer shaft 82 or a flexible shaft 108. The flexibility of the shaft 108 permits drilling in tight glenoid cavities 70. The flexible shaft 108 includes a quick-connect chuck 110 which receives the quick-connect drill bit 106. The drill bit 106 is sized such that when the chuck 110 of the flexible shaft 108 contacts the drill template 98, the appropriate hole depth for the superior hole 104 is achieved, thereby preventing the surgeon from drilling too deeply into the scapula 72.

Figure 4A:
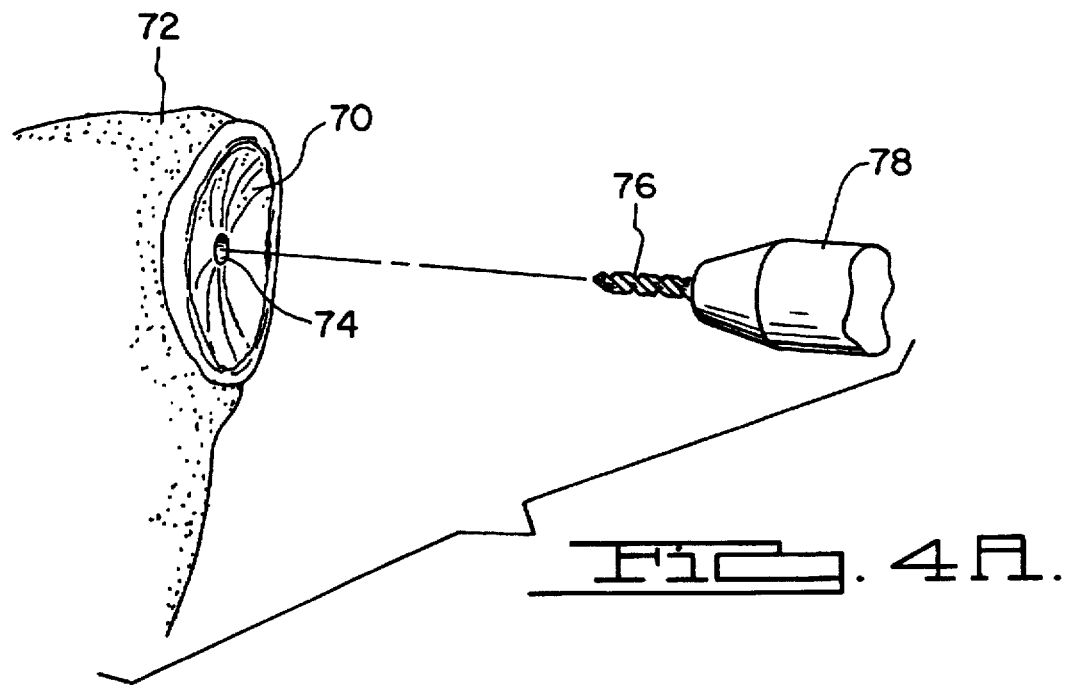
FIGS. 4A–4D illustrate a method for implanting the glenoid component using associated surgical components according to the teachings of the preferred embodiment of the present invention.
Figure 4B:
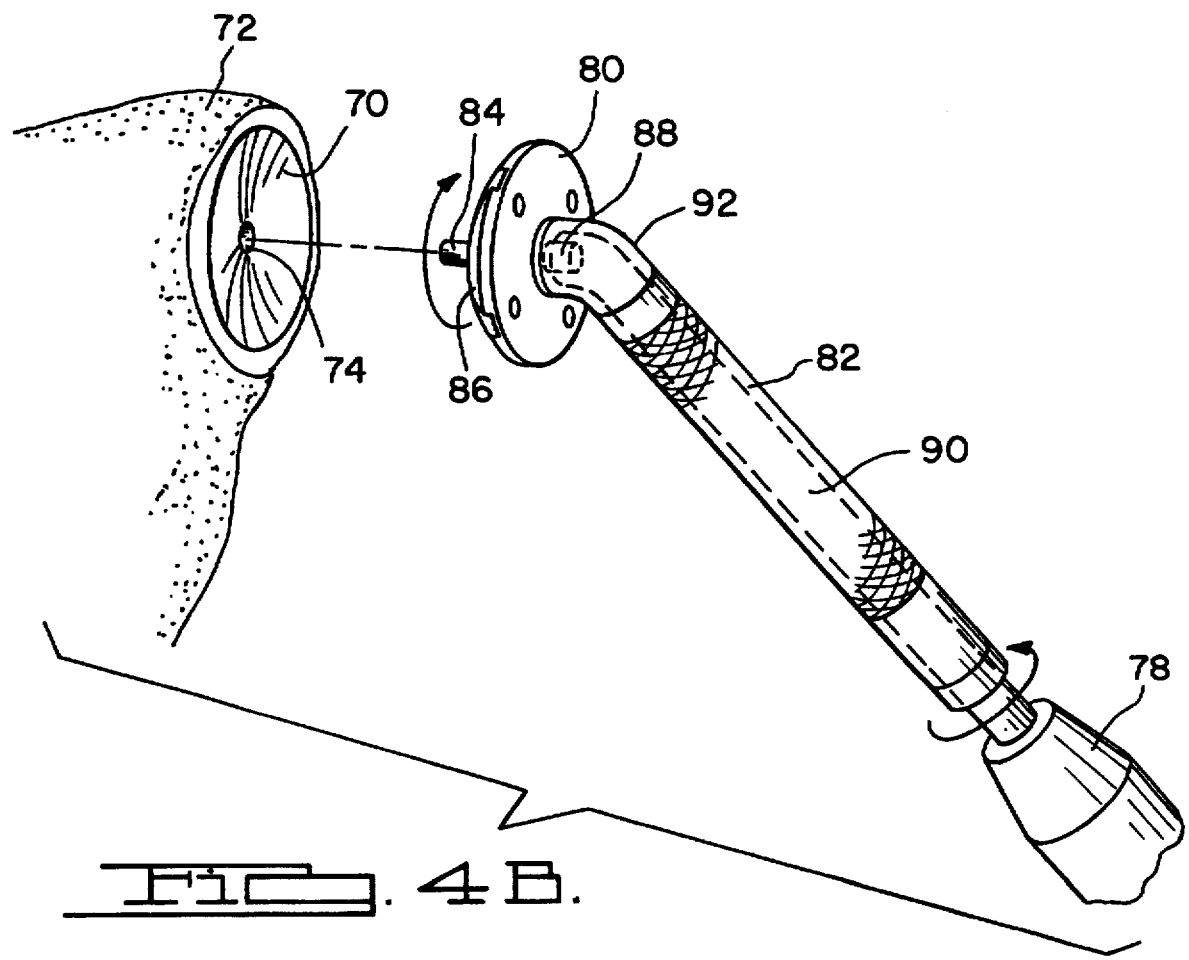
Figure 4C:
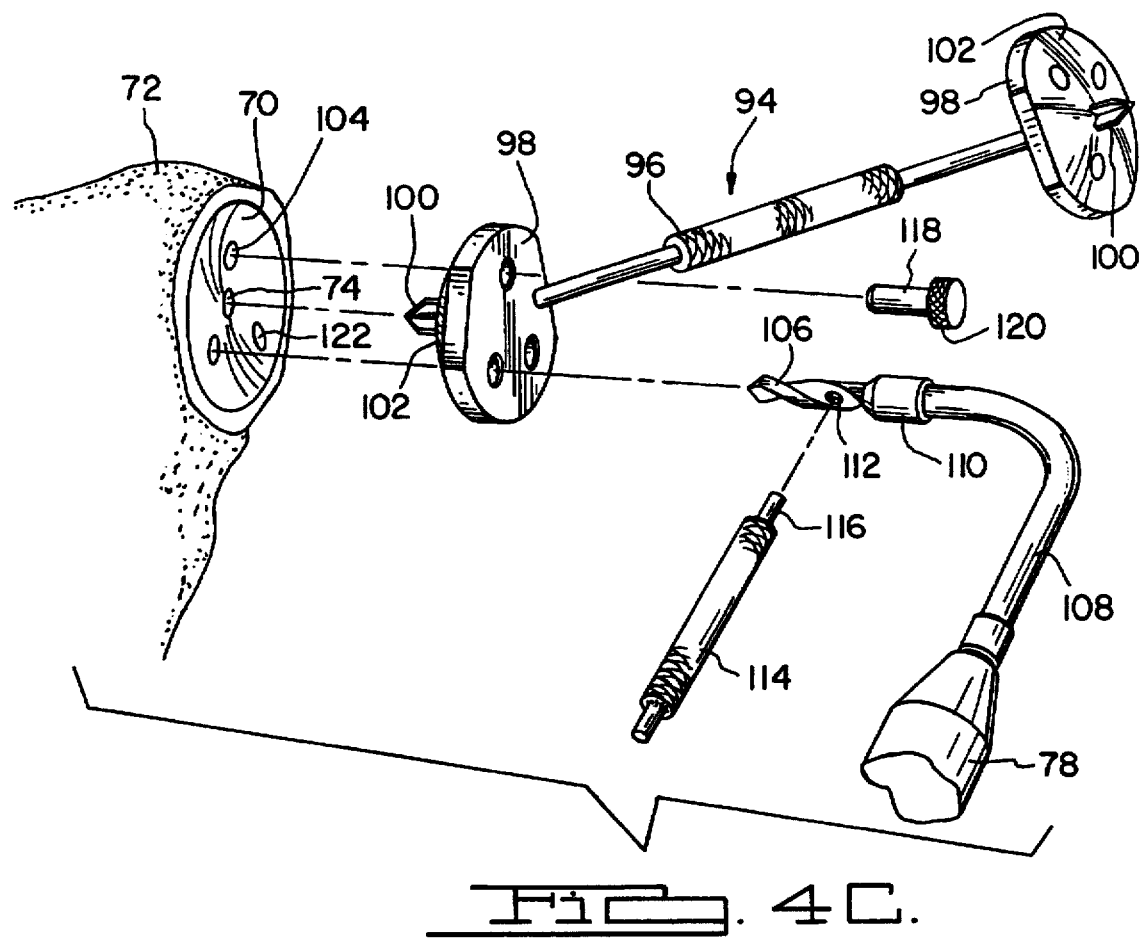
Figure 4D:
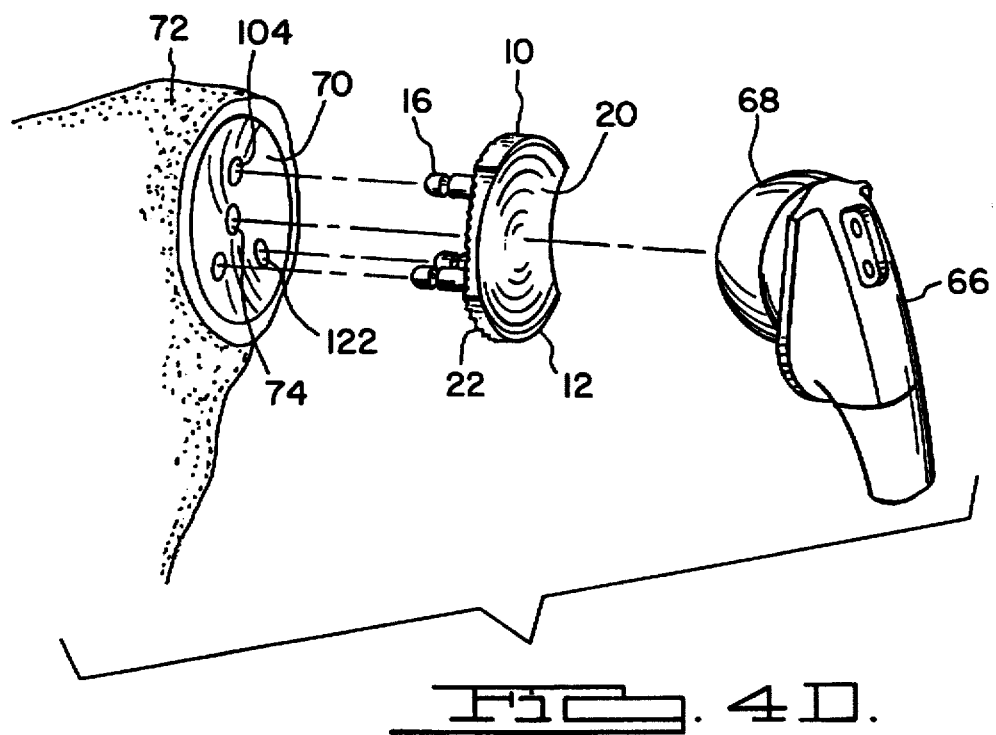

If the drill bit 106 is designed to be used with the angled shaft 82, the drill bit 106 will be threaded and will also include a hole 112, such as that shown in FIG. 4C, passing therethrough for receipt of a removal tool 114. To remove the threaded drill bit 106 from the angled reamer shaft 82, a tip 116 of the removal tool 114 is inserted into the hole 112 and rotated, thereby loosening the threaded drill bit 106. Alternately, if the quick release drill bit 106 is utilized with the quick-connect chuck 110 of the flexible shaft 108, the drill bit 106 is removed by simply using the quick-connect mechanism.

Once the superior hole 104 has been drilled, an alignment pin 118 having a knurled shoulder 120 may be inserted through the drill template 98 to further secure the drill guide 94 relative to the scapula 72 prior to drilling the inferior holes 122. The inferior holes 122 are then drilled in the same manner as the superior hole 104. Once the inferior holes 122 are drilled, the alignment pin 118 is removed from the superior hole 104 along with the drill guide 94, thereby exposing the superior hole 104 and the inferior holes 122. It should further be noted that various other drill guides may also be employed.

Once the cavities or holes 104 and 122 have been drilled, a provisional glenoid component (not shown) may be used prior to cementing the glenoid component 10 to verify hole placement, range of motion and appropriate glenoid size. After the proper size glenoid component 10 has been selected, cement is inserted into the superior hole 104, the inferior holes 122 and the pilot hole 74, in addition to being placed on the medial surface of the scapula 72 and the medial surface 22 of the glenoid component 10. The pegs 16 of the glenoid component 10 are then inserted into the holes 104 and 122 until the medial cement spacers 36 engage the scapula 72 to insure a uniform and proper thickness for the cement mantle. The glenoid component 10 is then held in place until the cement cures to secure the glenoid component 10 in the scapula 72. The head portion 68 the humeral component 66 may then engage the articulating surface 20 of the glenoid component 10.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A glenoid component for use in shoulder arthroplasty, said glenoid component adapted to be implanted into a scapula and engaged by a head of a humeral component, said glenoid component comprising:
   a body having a first articulating surface and a second textured medial surface opposite said first articulating surface, said first articulating surface adapted to be engaged by the head of the humeral component and said second textured medial surface adapted to be secured to the scapula;
   a plurality of circular base members extending from said second textured medial surface, each of said circular base members providing a circular base pad having a first diameter; and
   a plurality of cylindrical pegs, each of said cylindrical pegs having a first end adapted to engage a cavity formed in the scapula and a second end extending from one of said circular base members, each of said cylindrical pegs partially defined by a sidewall having a second diameter, wherein said first diameter of said circular base pegs is larger than said second diameter of said cylindrical pegs to increase peg shear strength without having to enlarge each cavity formed in the scapula to accommodate a larger second diameter of said cylindrical pegs.

2. The glenoid component as defined in claim 1 wherein said first articulating surface has a spherical concave surface adapted to permit rotational and translational movement of the head of the humeral component.

3. The glenoid component as defined in claim 2 wherein said spherical concave surface has an offset center to provide for a thicker superior portion relative to a thinner inferior portion to reduce superior dislocation of the head of the humeral component.

4. The glenoid component as defined in claim 1 wherein said second textured medial surface has a spherical convex shape and includes an enhanced textured surface over substantially the entire medial surface.

5. The glenoid component as defined in claim 4 wherein said enhanced textured surface includes a plurality of first parallel grooves positioned substantially perpendicular to a plurality of second parallel grooves to form a plurality of truncated pyramids that substantially increases an overall medial surface area.

6. The glenoid component as defined in claim 1 wherein each of said first ends of said cylindrical pegs have a semi-spherical shape.

7. The glenoid component as defined in claim 6 wherein each of said second ends of said cylindrical pegs has a radius about the circumference of said second end which blends into one of said circular base pads to define an annular portion about the second end of the cylindrical peg to increase the overall shear strength of said cylindrical peg.

8. The glenoid component as defined in claim 7 wherein each of said cylindrical pegs includes at least one outbound groove about the circumference of said cylindrical peg to provide a locking mechanism.

9. The glenoid component as defined in claim 1 wherein said plurality of cylindrical pegs includes a first superior cylindrical peg and a pair of second inferior cylindrical pegs, each cylindrical peg positioned on said second textured medial surface to form the corners of an isosceles triangle, thereby providing rotational and translational stability with a minimum amount of cylindrical pegs.

10. The glenoid component as defined in claim 1 wherein said body is defined by an outer peripheral sidewall which is generally pear-shaped and includes a curved superior portion, a curved inferior portion, a first planar portion and a second planar portion.

11. The glenoid component as defined in claim 1 wherein said body includes a plurality of medial cement spacers extending from said second textured medial surface to enable a uniform cement mantle to be formed.

12. The glenoid component as defined in claim 11 wherein each medial cement spacer is operable to be removed from said glenoid component.

13. A set of surgical components for use in shoulder arthroplasty, said set of surgical components comprising:
   a glenoid component adapted to be implanted into a scapula and engaged by a head of a humeral component, said glenoid component including,
   a body having a first spherical articulating surface and a second textured medial surface, said first spherical articulating surface adapted to permit rotational and translational movement of the head of the humeral component and said second textured medial surface being textured substantially over the entire medial surface to define a plurality of truncated pyramids,
   a plurality of circular base members extending from said second textured medial surface, each of said circular base members providing a circular base pad having a first diameter, and
   a plurality of cylindrical pegs, each of said cylindrical pegs having a first semi-spherical end adapted to engage a cavity formed in the scapula and a second circumferentially radiused end extending from one of the circular base pads to define an annular portion on said circular base pad, each of said cylindrical pegs includes a sidewall having a second diameter, wherein said first diameter of said circular base pegs is larger than said second diameter of said cylindrical pegs to increase peg shear strength.

14. The set of surgical components as defined in claim 13 wherein each of said cylindrical pegs includes an outbound groove about the circumference of said cylindrical peg to provide a cement locking mechanism.

15. The set of surgical components as defined in claim 13 wherein said plurality of cylindrical pegs includes a first superior cylindrical peg and a pair of second inferior cylindrical pegs, each cylindrical peg positioned on said second textured medial surface to form the corners of an isosceles triangle, thereby providing rotational and translational stability with a minimum amount of cylindrical pegs.

16. The set of surgical components as defined in claim 13 wherein said body is defined by an outer peripheral sidewall which is generally pear-shaped and includes a curved superior portion, a curved inferior portion, a first planar portion and a second planar portion.

17. The set of surgical components as defined in claim 13 further comprising a drill guide having a plug located on a spherical medial side adapted to prevent rotation of said drill guide upon engaging the plug with the scapula.

18. The set of surgical components as defined in claim 17 wherein said drill guide includes a first drill template affixed to a first end of said drill guide and a second drill template affixed to a second end of said drill guide.

19. The set of surgical components as defined in claim 13 further comprising a threaded drill bit having a hole passing therethrough for receipt of a tip of a removal tool.

20. The set of surgical components as defined in claim 13, wherein said body of said glenoid component further includes at least three medial cement spacers positioned on said second textured medial surface which extend beyond said second textured medial surface to provide for a uniform cement mantle.

21. A method for implanting a glenoid component during shoulder arthroplasty, said method comprising the steps of:
    drilling a center pilot hole in a glenoid cavity of a scapula;
    inserting a guide pin of a glenoid surface rasp into the center pilot hole;
    rotating the glenoid surface rasp to prepare a spherical surface on the glenoid cavity;
    inserting a pointed cruciate positioned on a medial surface of a drill guide into the pilot hole to secure the drill guide to the scapula;
    drilling a plurality of holes in the scapula using a drill template of the drill guide;
    providing a glenoid component having a body, a plurality of circular base members and a plurality of cylindrical pegs, said body having a first articulating surface and a second textured medial surface, each of said circular base members extend from and fill-in a portion of said second textured medial surface to provide a circular base pad having a first diameter and being substantially flush with said second textured medial surface, each of said cylindrical pegs extending from a circular base pad and adapted to engage the hole drilled in the scapula, each of said cylindrical pegs having a second diameter, said first diameter being larger than the second diameter;
    inserting cement into the plurality of holes drilled in the glenoid cavity, on the spherical surface of the glenoid cavity and on the second textured medial surface of the glenoid component; and
    inserting the glenoid component into the glenoid cavity of the scapula by inserting the plurality of pegs into the plurality of holes and securing the second textured medial surface to the spherical surface of the glenoid cavity.

22. The method as defined in claim 21 wherein the step of inserting the glenoid component into the glenoid cavity includes the step of engaging a plurality of medial cement spacers to the glenoid cavity to produce a uniform cement mantle.

23. The method as defined in claim 21 wherein the step of inserting the glenoid component into the glenoid cavity includes the step of removing a plurality of medial cement spacers from the glenoid component.

24. The method as defined in claim 21 wherein the step of drilling a plurality of holes in the scapula using the drill guide as a drill template further includes the step of inserting an alignment pin in one of the plurality of holes drilled in the scapula.

25. The method as defined in claim 24 wherein the step of providing a plurality of circular base members and a plurality of cylindrical pegs further includes the steps of providing each cylindrical peg having a first semi-spherical end adapted to engage a hole formed in the scapula and a second end having an arcuate bevel about a circumference of the second end that extends from one of the circular base members, wherein the second end having the arcuate bevel about the circumference of the second end and said first diameter being larger than said second diameter increases peg shear strength without having to provide a larger cylindrical peg diameter.

26. A glenoid component for use in shoulder arthroplasty, said glenoid component adapted to be implanted into a scapula and engaged by a head of a humeral component, said glenoid component comprising:
    a body having a first articulating surface and a second textured medial surface opposite said first articulating surface, said first articulating surface adapted to be engaged by the head of the humeral component and said second textured medial surface adapted to be secured to the scapula;
    a plurality of cylindrical pegs, each of said cylindrical pegs adapted to engage a cavity formed in the scapula; and
    a plurality of medial cement spacers, each of said medial cement spacers positioned on said second textured medial surface and extend beyond said second textured medial surface, wherein said plurality of medial cement spacers is adapted to provide a uniform cement mantle between the scapula and said second textured medial.

27. The glenoid component as defined in claim 24 further comprising a plurality of circular base members extending from said second textured medial surface, each of said circular base members providing a circular base pad having a first diameter, each of said cylindrical pegs having a second diameter, wherein said first diameter of said circular base pads is larger than said second diameter of said cylindrical pegs to increase peg shear strength.

* * * * *

UNITED STATES PATENT AND TRADEMARK OFFICE
CERTIFICATE OF CORRECTION

PATENT NO.   : 5,800,551
DATED        : September 1, 1998
INVENTOR(S)  : Daniel E. Williamson et al.

It is certified that error appears in the above-identified patent and that said Letters Patent is hereby corrected as shown below:

Column 7,
Line 23, "extending from" should be -- forming a portion of --.
Line 26, after "diameter" insert -- and a height that does not substantially extend beyond a maximum height of said second textural medial surface --.
Line 33, "pegs" should be -- pads --.
Line 43, "an offset" should be -- a --.
Line 43, after "center" insert -- which is offset relative to the geometric center of the body --.
Line 67, delete "outbound".

Column 8,
Line 23, after "comprising:" insert -- a humeral component; and --.
Line 25, "a" should be -- said --.
Line 34, "extending from" should be -- forming a portion of --.
Line 37, after "diameter," insert -- and a height that does not substantially extend beyond a maximum height of said second textured medial surface --.
Line 41, delete "circumferentially radiused".
Line 42, delete "to define an annular portion on said circular base pad, --.
Line 45, "pegs" should be -- pads --.
Line 47, after "strength" insert -- and define an annular portion on said circular base pads about said cylindrical pegs --.

Column 9,
Line 29, delete "extend from and fill-in a portion of" and insert -- forming a portion of --.
Line 31, delete "being substantially flush with" and insert -- a height that does not substantially extend beyond a maximum height of --.
Line 36, "the" should be -- said --.

UNITED STATES PATENT AND TRADEMARK OFFICE
CERTIFICATE OF CORRECTION

PATENT NO. : 5,800,551
DATED : September 1, 1998
INVENTOR(S) : Daniel E. Williamson et al.

It is certified that error appears in the above-identified patent and that said Letters Patent is hereby corrected as shown below:

Column 10,
Line 32, after "scapula;" insert -- a plurality of circular base members forming a portion of said second textured medial surface, each of said circular base members having a first diameter and a height that does not substantially extend beyond a maximum height of said second textured medial surface --.
Line 33, before "each" insert -- having a second diameter, said first diameter of said circular base members being larger than said second diameter of said cylindrical pegs".
Line 34, before "adapted" insert -- extend from one of said circular base members and is --.
Line 43, delete Claim 27.

Signed and Sealed this

Second Day of July, 2002

Attest:

Attesting Officer

JAMES E. ROGAN
Director of the United States Patent and Trademark Office